United States Patent
Wentworth et al.

[11] Patent Number: 6,133,740
[45] Date of Patent: Oct. 17, 2000

[54] CHLORINE SPECIFIC GAS CHROMATOGRAPHIC DETECTOR

[75] Inventors: Wayne E. Wentworth, Pearland; Stanley D. Stearns, Houston, both of Tex.

[73] Assignee: Valco Instrument Co., Inc, Houston, Tex.

[21] Appl. No.: 08/593,827

[22] Filed: Jan. 30, 1996

[51] Int. Cl.[7] .......................... G01N 27/62; G01N 27/68
[52] U.S. Cl. ............... 324/464; 324/449; 324/123 R; 324/455; 73/28.02
[58] Field of Search .................... 324/449, 450, 324/452, 455, 464, 123, 71.4; 73/23.4, 23.35, 28.02; 313/231.4, 231.7; 315/111.01, 111.91; 250/379, 385.2; 436/153

[56] References Cited

U.S. PATENT DOCUMENTS

| | | | |
|---|---|---|---|
| 3,934,193 | 1/1976 | Hall | 324/439 |
| 4,555,383 | 11/1985 | Hall | 324/449 X |
| 5,153,519 | 10/1992 | Wentworth et al. | 324/464 |
| 5,317,271 | 5/1994 | Wentworth et al. | 324/464 |
| 5,394,090 | 2/1995 | Wentworth et al. | 324/464 |
| 5,394,091 | 2/1995 | Wentworth et al. | 324/464 |
| 5,394,092 | 2/1995 | Wentworth et al. | 324/464 |
| 5,541,519 | 7/1996 | Stearn et al. | 324/464 |

*Primary Examiner*—Kenneth A. Wieder
*Assistant Examiner*—Diep Do

[57] ABSTRACT

A method and apparatus are set forth which enables a gas chromatographic column output to be connected with a pulse discharge chamber in which chemically bound chlorine in volatile organic or inorganic samples is measured. A spark discharge is formed in the chamber to ionize and excite helium molecules to a metastable state. In turn, that transfers excitation to a trace of krypton gas in the chamber which is ionized, and the ionized krypton then preferentially binds with chemically bound chlorine. The latter binding occurs with the liberation of a photon centered at about 222 nanometers thereby defining a spectral region of interest which is measured by a photomultiplier tube to quantify chemically bound chlorine.

25 Claims, 1 Drawing Sheet

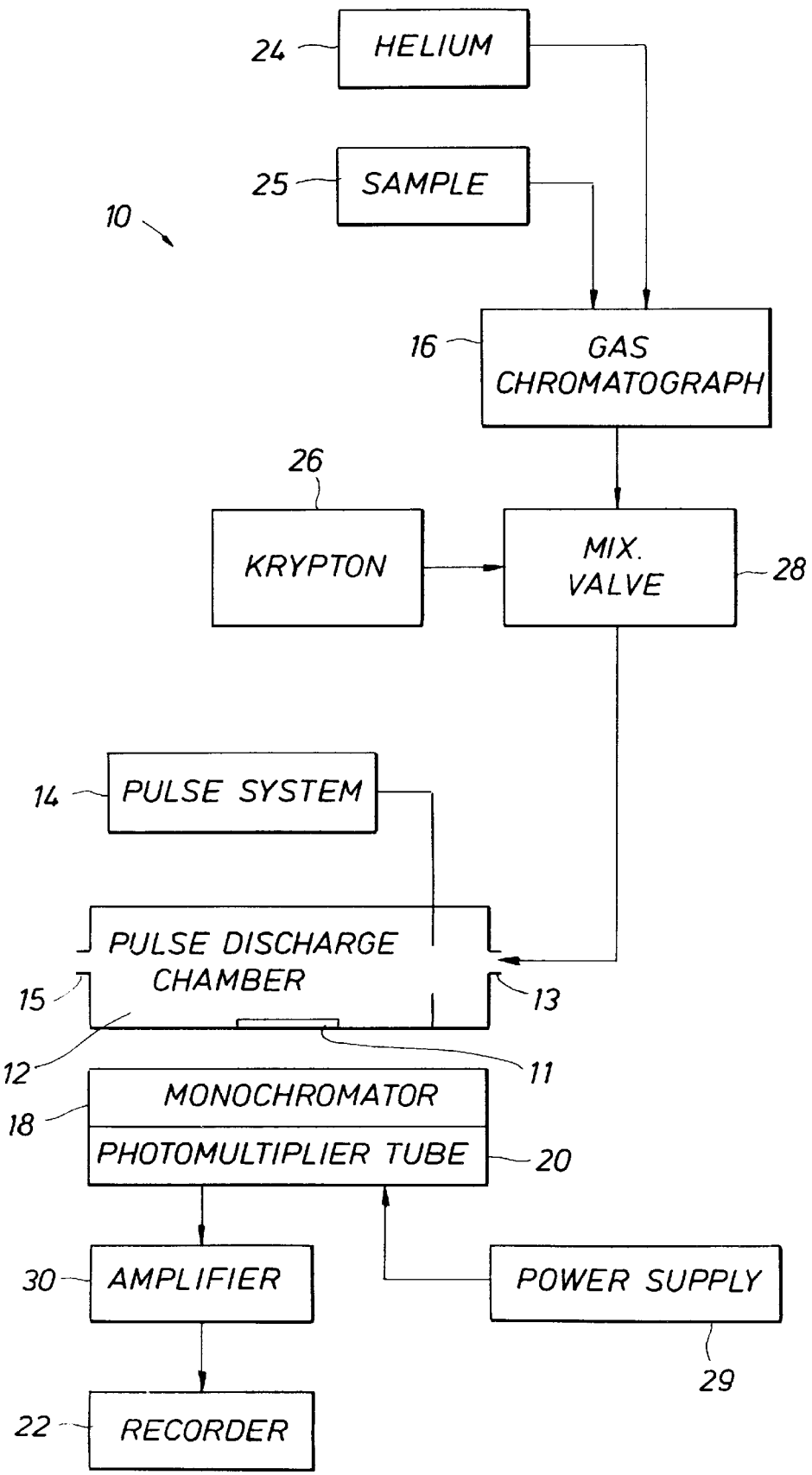

CHLORINE SPECIFIC GAS CHROMATOGRAPHIC DETECTOR

BACKGROUND OF THE DISCLOSURE

This disclosure is directed toward the measurement of concentrations of compounds in a gas sample. More particularly, the disclosure is directed toward methods and apparatus for measuring concentrations of compounds containing chlorine within a mixture of noble gases and, in particular, within a helium carrier gas which has been doped with relatively small concentrations of krypton. The disclosed system has also been used for measuring concentrations of other halogens such as fluorine. Other noble gas dopants such as xenon and argon have also been employed. Spark discharges are used to initiate a series of reactions within the carrier gas and sample mixture which results in the formation of an excited chlorine-krypton molecule which, in turn, emits characteristic photon radiation. The concentration of chlorine within the sample is then determined from the measured intensity of the characteristic photon radiation from the decay of excited chlorine-krypton. It is emphasized that the intensity of the characteristic photon radiation is proportional to the mass of chlorine within the sample. The chlorine content is, therefore, determined independently of the structure of the compound in which it is contained.

For many years, there has been a strong desire to develop gas chromatographic detectors that detect only a specific element. It is well known in the art that a gas chromatographic (GC) column is able to separate very similar compounds into separate peaks output as a function of time. This time-based separation is especially useful in delineation of adjacent peaks. Once the peaks are separated, it is necessary to identify the constituents of the peaks, and then to quantify these constituents so that concentrations of compounds or elements within the sample gas input into the GC can be determined.

Detectors which respond to chlorine are especially needed in the field of pollution monitoring and control. Chlorine pollutants in air or in water are generally in the form of organic compounds. Pollutants, however, also include a far greater variety of compounds which have chlorine in them. Common, and potentially dangerous, water and air pollutants include gaseous freons, pesticide residue in the soil, polychlorobiphenyl (often called PCB) and many others. While all of these can be extremely valuable compounds in one aspect, they can also be detrimental in trace quantities where they are not wanted. They are especially difficult to isolate, quantify and remove in trace quantities. Even trace quantities of these materials can pose significant environmental hazards in air, water, and soil.

Detectors which respond to trace amounts of chlorine are also needed in many chemical processes which utilize catalysts. Even trace amounts of chlorine can deteriorate or even destroy catalysts. As an example, in the crude oil refining industry, concentrations of chlorine as low as ten parts per million can essentially destroy or "poison" the catalyst used in refineries which produce gasoline.

SUMMARY OF KNOWN PRIOR ART

Various techniques have been used to measure trace quantities of materials, and in particular, traces of the element chlorine or chlorine compounds in air, water and soil samples.

There are numerous "wet chemistry" techniques known in the art for detecting chlorine. As a group, these techniques are time consuming, relatively expensive, and certainly not suited for on-line, real-time monitoring of trace chlorine content.

U.S. Pat. No. 5,019,517 to Dale M. Coulson discloses a detector system and method for detecting trace gases. The detection system is especially suited for detecting a halogen containing component in a gas stream, and includes a gas chromatograph which is connected by a gas line to a pyrolysis chamber. Sources of additional gas streams are connected by a second gas line to the pyrolysis chamber. The system features a temperature control feedback system which maintains the temperature of the pyrolysis chamber independent of the detector electrodes and at a temperature between about 700 and 1,000 degrees Centigrade (°C.). U.S. Pat. No. 4,440,726 to Dale M. Coulson discloses an electrochemical detector cell which is sensitive to trace elements including chlorine and chlorine compounds. These techniques are usually slow, require apparatus which is relatively expensive to fabricate, operate and maintain. In addition, the apparatus associated with these techniques are relatively large physically, and the actual measurements are compound-specific. Test standards of the EPA are similar to the Coulson process mentioned above.

Other techniques have been used to monitor crude oil for trace amounts of chlorine prior to feeding the crude stock to a refinery. A particular nuclear technique is described in U.S. Pat. Nos. 4,200,789 and 4,209,695 to Dan M. Arnold, et al wherein thermal neutron capture is used to detect elemental chlorine concentrations as low as 5 parts per million (ppm). The apparatus required to make this measurement is quite large, and is also expensive to fabricate. In addition, the isotopic source of neutrons requires significant radiation control and safety procedures.

An electrolytic conductivity detector (ELCD), known in the art as the Hall detector, has been used to detect very small quantities of compounds containing elements such as sulfur and nitrogen. This technology is taught in U.S. Pat. Nos. 3,934,193 and 4,555,383 to R. C. Hall. Hall's teachings of chlorine compound detection is limited to the detection of chlorinated hydrocarbons such as pesticides.

Detection devices consisting of a pulse discharge chamber have been used to detect very small elemental concentrations, including chlorine. This type of detection device is exemplified by the disclosures of U.S. Pat. Nos. 5,153,519 and 5,317,271 to Stanley D. Stearns and Wayne E. Wentworth, both of which are assigned to the assignee of the present disclosure. Selective sample ionization and element-specific photon radiation, both generated by continuous or pulsed spark discharges, are used to determine quantitatively elements and compounds of interest within a sample. As an example, chlorine can be detected by the direct excitation of chlorine which decays by the emission of relatively intense radiation at a characteristic wavelength of approximately 138 nanometers (nm). This emission is resolved from other radiations generated within the pulse discharge chamber by means of a monochromator or other suitable spectrographic device. Since air is not transparent to radiation of wavelength less than approximately 200 nm, the monochromator of other spectrographic devices must be operated under vacuum conditions. Likewise, the "window" within the pulse discharge chamber through which the 138 nm emerges and impinges upon the monochromator must also be transparent to this radiation of interest. Relatively inexpensive quartz can not be used as a window material since it is only transparent to radiation above 200 nm. Instead, generally more expensive materials, such as magnesium fluoride, must be used as the chamber window material.

SUMMARY OF THE INVENTION

One objective of the invention is to provide a chromatographic detector system which responds specifically to the element chlorine, or to any compounds containing the element chlorine. A further objective of the invention is to provide a detection system which can detect chlorine in amounts as small as 1 picogram (pg), and which responds linearly to the amount of chlorine within a sample over at least three orders of magnitude. A still further objective of the invention is to provide a system which can measure concentrations of other halogens. A still further goal of the invention is to provide a chlorine specific detection system which is relatively inexpensive to fabricate and maintain, physically compact and rugged, and relatively easy to operate. This objective includes a detection system which utilizes a spectrographic system such as a monochromator which can be operated in air at atmospheric pressure.

The present disclosure sets forth a chlorine specific detection system which meets the foregoing objectives, and which provides additional advantages that will become apparent in the following disclosure. The system can also be used to measure concentrations of other halogens. The system is especially successful in detecting and quantifying chlorine in the form of both volatile organic and inorganic chlorine compounds, as well as chlorine gas. The sample is commingled in a mixture of noble gases. More specifically, a small concentration of krypton (Kr) gas, referred to as a "dopant", is added to the output from a GC, which contains the suspected chlorine sample of interest dispersed in a helium (He) carrier gas. Alternately the Kr dopant can be added to the carrier gas to the GC. The carrier gas is typically "doped" with 1.0% to 5.0% Kr, and preferably with approximately 1.0% Kr. Tests have shown that the concentration of Kr dopant does not affect the quantitative Cl measurement if the concentration exceeds 0.2% threshold level. This aspect will be discussed further in a subsequent section of this disclosure. The mixture of Kr doped helium carrier gas, which also contains the chlorine sample to be detected and quantified, is next passed into a spark discharge chamber in which various components of the gas are ionized and excited with an electrical spark discharge. The spark discharge can be either continuous or pulsed. Specifically, the spark discharge produces $He^+$ and $He_2^+$ ions. These $He^+$ and $He_2^+$ ions then react with the Kr dopant atoms to produce krypton ions, $Kr^+$, and one or two He. Defining a generic molecule containing chlorine as "RCl" where "R" represents one or more additional elements, the $Kr^+$ ion then reacts with the RCl molecule to form the excited molecule KrCl* and the ion $R^+$. The excited molecule KrCl* decays to the ground state by the emission of characteristic photon radiation in a band centered about a wavelength of 222 nm. Throughout the remainder of this disclosure, the emission of photon radiation will be referred to as an emission at 222 nm, but it should be understood that the emission is encompassed by a narrow band of wavelengths which is centered at 222 nm. This particular reaction is discussed in the publication "Comparison of the $Rg^+(^2P_{1/2})/Cl^-/He$ and $Rg^+$ $(^2P_{3/2})/Cl^-/He$ three-body ionic-recombination reactions for the formation of RgCl*, Rg* and Cl*", Masaharu Tsuji et al, Chem. Phys., 94(6), 4291 (1991).

Assuming that the Kr dopant concentration exceeds the 0.2% threshold, the intensity of the emitted 222 nm photon radiation is proportional to the amount of compound RCl in the sample, and more specifically, proportional to the amount of elemental chlorine contained as sample in the Kr doped, helium carrier gas output from the GC column. The pulse discharge chamber incorporates a window or port which is transparent to photon radiation at 222 nm. Quartz is a suitable window material which meets this transparency requirement for the radiation of interest at 222 nm. If the detection system is used to detect emissions below 200 nm, window material transparent to these emissions, such as magnesium fluoride ($MgF_2$), must be used. Photon radiation emerges from the ionization chamber through the window, and into a monochromator which disperses the photon radiation generated within the ionization chamber. The monochromator therefore provides a means for isolating the 222 nm photon radiation resulting from the decay of excited KrCl from radiation of other wavelengths which might be generated within the pulse discharge chamber. The intensity of 222 nm photon radiation delineated or resolved in the monochromator is then measured with a photomultiplier detection system featuring a photomultiplier tube and associated amplification and power circuitry. The output of the photomultiplier detection system is, therefore, proportional to the amount of chlorine in the gas which is input into the pulse discharge chamber. The photomultiplier detection system output, which is typically an electrical current, can be converted to quantitative measures of sample chlorine content by using a calibration conversion constant. This calibration conversion constant is determined by measuring the output current of the photomultiplier detector system using samples containing known amounts of chlorine, again assuming that the Kr dopant concentration exceeds the previously mentioned 0.2% threshold concentration.

The present detection system offers many advantages over prior art systems. The photon radiation centered about 222 nm from excited KrCl is easily measured using the previously described photomultiplier detection system. Furthermore, air is transparent to the 222 radiation thereby allowing the monochromator used to isolate the photon radiation from chlorine to be operated with air at atmospheric pressure. Furthermore, relatively inexpensive quartz can be used as window material in the pulse discharge chamber. If however, the system is used to detect photon radiations below 200 nm resulting for other emissions, air is no longer transparent to radiations of these wavelengths, therefore, the monochromator must be operated in a vacuum. Previously referenced detectors, which also employ pulse discharge chambers as disclosed U.S. Pat. Nos. 5,153,519 and 5,317,271, can excite elemental chlorine. The emission from excited chlorine occurs at wavelengths ranging from approximately 130 nm and into the UV-visible region. The atomic emission at the low wavelength of approximately 138 nm is intensive, and elemental chlorine concentration can be determined from a measure of this photon radiation. In such a measurement, however, the monochromators required to disperse radiation at this wavelength must be devoid of air, since air absorbs radiation at this wavelength. Commonly, these monochromators are put under vacuum using vacuum pumping in order to eliminate the air. This adds significantly to the cost, size, complexity and operating expense of such a prior art detection system. Furthermore, quartz is not transparent to radiation at this wavelength. Windows for the pulse discharge chamber made of material transparent at 138 nm, such as magnesium fluoride, must be used in the spark discharge chamber. Magnesium fluoride is considerably more expensive to obtain and to fabricate than quartz, thereby further increasing the cost of such an elemental chlorine detector.

Turning again to the present detection system, studies have shown that, for a given Kr dopant level exceeding the threshold concentration of 0.2%, the sensitivity of the device is as low as 1 to 2 pg of chlorine. Studies have further shown that the output of the photomultiplier detection system is linear with sample chlorine content over at least three orders of magnitude. Many chlorine compounds of interest also contain carbon, such as carbon tetrachloride ($CCl_4$). Furthermore, many of the chlorine compounds of interest are found in hydrocarbons, thus much carbon is present, from other sources such as gasoline, in the sample to be analyzed. Carbon will therefore also be excited within the pulse discharge chamber in addition to excited chlorine as KrCl*. Excited atomic carbon emits photon radiation at wavelengths of 193.1 and 247.9 nm. The monochromator and associated photomultiplier detector system can easily resolve the 222 nm radiation of interest from the "interfering" photon radiation from carbon.

To briefly summarize, the present chlorine specific detection system is very sensitive and is a simple system to operate once the various components have been assembled. It utilizes two sources of noble gas (as a carrier gas system) in which the sample gas containing chlorine is dispersed. The primary noble gas is helium which is the carrier gas for a GC column and contains the chlorine compound. The trace or dopant gas is krypton which is added to the mixture of helium carrier and sample gas. This mixture is then input into the pulse discharge chamber. The spark discharge can be either pulsed or continuous. The discharge creates excited KrCl through the reaction sequence previously discussed. Radiation from the decay of excited KrCl is detected with a photomultiplier detection system which utilizes a monochromator operating in air at atmospheric pressure. The output of this detection system is used to determine the concentration of chlorine within the sample. It is emphasized that the detection system responds to the mass of chlorine in the sample independent of the structure of a compound. As an example, $CCl_4$ induces four times the detector response than does $CH_3Cl$.

While the foregoing summarizes a number of aspects of the present disclosure, the detailed description will set forth the preferred embodiment. That will be understood in conjunction with or in reference to the attached drawings.

BRIEF DESCRIPTION OF THE DRAWING

So that the manner in which the above recited features, advantages and objects of the present invention are attained and can be understood in detail, more particular description of the invention, briefly summarized above, may be had by reference to be embodiments thereof which are illustrated in the appended drawing.

The single drawing is a schematic block diagram of the detection apparatus of the present disclosure, and sets forth a pulse discharge chamber which has input from a source of an unknown sample, typically a gas chromatographic column, and which exposes a Kr trace gas and He carrier gas to a pulse discharge to thereby create metastable molecules which emit a photon at a particular frequency for quantification of any chlorine which may be present in the sample.

DETAILED DESCRIPTION OF THE PREFERRED EMBODIMENT

The preferred embodiments of the system will be presented in two sections. The first section will disclose in detail the detection system apparatus and further, the key elements of the detection system apparatus. The second section will present in detail the series of reactions which occur within the pulse discharge chamber which eventually lead to the emission of photon radiation characteristic of the decay of KrCl excitement. The detection of this radiation is, as outlined previously, the means by which the chlorine content of the sample is determined.

APPARATUS

Attention is directed to the only view which identifies a test system in block diagram form with the numeral 10. The test system utilizing a pulse discharge chamber 12. The pulse discharge chamber is a device of the sort described, for example, in FIG. 2 of U.S. Pat. No. 5,153,519 and also exemplified in U.S. Pat. No. 5,317,271, both of which are assigned to the assignee of the present disclosure. The pulse discharge chamber utilizes a current pulsing system 14 which provides a spark across a pair of spaced, separated terminals or electrodes (not shown) in the pulse discharge chamber. Pulsed excitation as commonly used by steady state excitation of the gas flow is acceptable.

A mixture of gas is input into the pulse discharge chamber 12. There are several embodiments of the gas input system that will produce acceptable results from the disclosed chlorine detection system. The schematic illustrates helium carrier gas from a reservoir 24 being input into the gas chromatograph (GC) column 16 as a carrier gas. Sample containing the chlorine compound or compounds to be detected and quantified is input into the GC column 16 from a sample source 25. Gas eluted from the GC 16 is then flowed through a mixing valve 28. Krypton dopant gas from the reservoir 26 is also flowed into the mixing valve 28 where it is commingled with the helium carrier gas containing the unknown sample or samples of chlorine. Alternately, the dopant gas can be added to the carrier gas to the GC. It is also possible to buy helium in a large tank, either pure or mixed with trace amounts of other noble gases. If desired, the correct concentration of dopant can be mixed in the helium to reduce valving complexity. Typically, this gas mixture is then flowed into the inlet port 13 of the pulse discharge chamber 12 where it passes between the terminals of the pulse discharge chamber and exposed to a pulse discharge spark. The gas eventually exits the pulse discharge chamber 12 through the exit port 15 thereby giving a net flow of gas through the chamber from right to left as illustrated in the block diagram of the system. The gas which is exposed to the spark is excited. When that occurs, and long after the spark has ended, there remains a number of excited gas molecules as described in detail in the previously referenced U.S. Pat. Nos. 5,153,519 and 5,317,271, the descriptions which are entered herewithin by reference.

As discussed previously, the system produces, through a series of reactions within the pulse discharge chamber 12, photons from the decay of excited KrCl (KrCl*) which are used to identify and to quantify the chlorine in the sample material. The characteristic photon radiation from the decay of KrCl* is a band centered about a wavelength of 222 nm. Details of the reactions occurring within the pulse discharge chamber 12 will be presented in the next section of this disclosure.

The pulse discharge chamber 12 contains an optical window which is transparent to the 222 nm photon radiation emitted in the decay of KrCl excitement. Quartz is a material which meets this requirement. This window is identified by the numeral 11 and is depicted conceptually as being physically located in the side of the pulse discharge chamber 12. It should be understood that the optical window can be placed at a variety of locations in the pulse discharge chamber. As an example, in the previously referenced U.S. Pat. Nos. 5,153,519 and 5,317,271, it is disclosed that the optical window can even be located at the input orifice 13 of the pulse discharge chamber 12, or at any other position on the chamber where photon emission within the chamber 12 can be "viewed".

A monochromator 18 is positioned near the optical window 11 to receive photon emissions from the chamber. Air at atmospheric pressure is transparent to the 222 nm radiation from chlorine. The monochromator can, therefore, be operated in air at atmospheric pressure, and does not require the vacuum operation or controlled gas environment operation of prior art devices. The monochromator can be of the prism type wherein the angle of the prism is adjusted with respect to the incident photon radiation to resolve radiation of a specific energy which, in the chlorine detection system, is 222 nm. The 222 nm radiation exits the monochromator 18 and then impinges upon a photomultiplier tube (PMT) 20 which converts the photon signal to a corresponding electrical signal in a manner well known in the art. High voltage and B+ power supplies are shown conceptually as a power supply element 29. The current output from the PMT 20 is then amplified by means of the amplifier circuit 30 and subsequently recorded by the recorder 22. The intensity of the recorded current is proportional to the chlorine content within the pulse discharge chamber 12. By measuring the current using samples of known chlorine content, the current calibration constant for the photomultiplier detection system can be determined thereby allowing the measured current to be converted to corresponding absolute measures of chlorine in the sample.

Alternate means can be used to resolve the characteristic 222 nm photon radiation resulting from the KrCl excitement. In one alternate embodiment, the monochromator 18 contains a grating which is adjusted to pass only the characteristic KrCl radiation. This radiation is again detected by the PMT 20 and processed by the photomultiplier detection system as described previously. In a second alternate embodiment, the monochromator is replaced with an interference filter (not shown) which is again set to pass a band of photon radiation centered at 222 nm with a band width of, perhaps, +/−5 nm. Again the PMT detects the passed photon radiation and the photomultiplier detection system converts this signal to a corresponding optical signal in a manner previously discussed.

If the detection system is embodied such that additional photon radiation below approximately 200 nm is detected, then quartz is no longer transparent to the emitted radiation. Magnesium fluoride ($MgF_2$) is a suitable window material which is transparent to radiation below 200 nm. Likewise, the monochromator can no longer be operated in air at atmospheric pressure since air is not transparent to photon radiation below approximately 200 nm. The monochromator or any alternate spectrographic system must be operated under vacuum conditions.

PULSE DISCHARGE CHAMBER REACTIONS

Attention is now directed toward reactions which occur within the pulse discharge chamber and which eventually lead to the emission of radiation characteristic of the decay of excited KrCl to the ground state.

Krypton doped helium carrier gas passed through the electrical pulse discharge or spark produces $Kr^+$ by means of the reaction $$He_2^+ + Kr = Kr^+ + 2He \qquad (1)$$

A generic chlorine compound will be designated as "RCl" where "R" represents one or more elements forming the chlorine molecule. As an example, "R" would represent $CH_3$ in $CH_3Cl$. The $Kr^+$ ions then react with any chlorine compound, RCl, within the chamber yielding KrCl* through the reaction $$Kr^+ + RCl = KrCl^* + R^+. \qquad (2)$$

The excited molecule KrCl* then decays yielding $$KrCl^* \rightarrow KrCl + hv_{222} \qquad (3)$$

where $hv_{222}$ represents a narrow band of photon radiation centered about a wavelength of 222 nm.

Attention is again directed to the Kr dopant gas, and more specifically to the concentration of Kr required in the carrier gas to eventually yield the reaction of equation (3) wherein the intensity of $hv_{222}$ is truly a linear function of the concentration of RCl. For a given concentration of RCl, it has been found that $hv_{222}$ increases linearly with Kr concentration up to a Kr concentration of approximately 0.2%. Above 0.2%, the concentration of Kr is sufficient to deplete the $He_2^+$ of equation (1) and therefore the intensity of $hv_{222}$ ceases to be a function of increased Kr concentration. The desired concentration of dopant is greater than 0.2%, but perhaps less than 1.0% to minimize the operating cost of supplying Kr. Stated another way, if the Kr dopant concentration is above 0.2%, the yield of 222 nm photon radiation will be independent of the Kr concentration and vary only with the concentration of RCl, as desired. An oversupply of krypton above the threshold 0.2% level does not, however, seem to handicap the operation of the system.

Sensitivity of the chlorine detection device has been measured and has been found to be approximately 1 to 2 picograms of chlorine. The reason for this exceptionally high sensitivity apparently arises from the inherent high rate constant for an ion-molecule reaction such as the one depicted in equation (2). Furthermore, at concentrations of Kr dopant above the "saturation" level of 0.2%, the response of the system to concentrations of Cl has been found to be linear over at least three orders of magnitude which allows the previously discussed calibration constant, for converting output current from the photomultiplier detection system to absolute chlorine content, to be a simple multiplicative constant.

The reactions of equations (1) through (3) are certainly not representative of all of the reactions that can, and do, occur within the pulse discharge chamber 12. Many general classes of reactions that can occur have been tabulated in the previously referenced U.S. Pat. Nos. 5,153,519 and 5,317,271.

Attention will be directed to another reaction which has practical and commercial bearing on the operation of the chlorine detection system. Many chlorine compounds of interest also contain carbon, such as carbon tetrachloride ($CCl_4$). Furthermore, many of the chlorine compounds of interest are found in hydrocarbons, thus carbon is present, from other sources such as gasoline, in the sample to be analyzed. Carbon will therefore also be excited within the pulse discharge chamber 12, in addition to excited chlorine as KrCl*. Excited atomic carbon emits photon radiation at wavelengths of 193.1 and 247.9 nm. The monochromator 18 and associated photomultiplier detector system can easily resolve the 222 nm radiation of interest form the "interfering" photon radiation from carbon. It should be noted that emission from $C_2^*$ does fall very close the 222 nm wavelength and poses a potential interference to the chlorine emission. At low concentrations, however, $C_2^*$ emission should be weak since $C_2^*$ is formed by a second order reaction of carbon.

The response of chlorine to krypton initiated excitation is observed at 222 nanometers. The table below lists the response of both chlorine and fluorine to three noble gases (dopants) in the helium carrier gas. Each response is an observed emission wavelength in nanometers:

TABLE I

|          | argon | krypton | xenon |
|----------|-------|---------|-------|
| fluorine | 193   | 248     | 308   |
| chlorine | 174   | 222     | 308   |

The intensity for these responses is:

TABLE II

|          | argon    | krypton  | xenon  |
|----------|----------|----------|--------|
| fluorine | moderate | moderate | strong |
| chlorine | moderate | strong   | strong |

In addition, xenon dopant reacts with fluorine to yield a moderate response at 351 nm.

In the tabled data, xenon is not able to discriminate between the two halogens so it is less desirable.

The foregoing wavelength data shows that argon responses are below 200 nm in wavelength, and therefore are in a range at which air absorption is more likely to handicap intensity measurement. The tabled data therefore suggests preferred use of krypton provided sharp discrimination of the fluorine and chlorine emissions is implemented to separate signals at 222 and 248 nm. As a generalization, the krypton is the preferred dopant.

SUMMARY

To briefly summarize, the present chlorine specific detection system is a simple system to operate once the various components have been assembled. It utilizes two sources of gas in which the sample gas containing chlorine is dispersed. The primary noble gas is helium which is the carrier gas from a GC column and contains the chlorine compound. The trace or dopant gas is krypton which is added to the mixture of helium carrier and sample gas. This mixture is then input into the pulse discharge chamber. The discharge creates excited KrCl through the reaction sequence previously discussed. Radiation from the decay of excited KrCl is detected with a photomultiplier and monochromator detection system which can be operated in air at atmospheric pressure, and the output of this system is used to determine the concentration of chlorine within the sample.

The system has been found to be extremely sensitive to chlorine, and that the response of the system is linear with sample chlorine content over at least three orders of magnitude. Furthermore, photon radiation from most common "interfering" reactions that can occur within the pulse discharge chamber can be resolved from the desired radiation from the decay of excited KrCl using a monochromator, or alternately, by using a grating or an interference filter.

It has been found that the system can also be used to measure concentrations of other halogens. These concentrations are detected in the same methodology as is used to measure chlorine concentration, namely, by measuring radiation characteristic of the decay of a particular halogen compound. It has also been found that noble gases other than Kr can be used as a dopant.

While the foregoing is directed to the preferred embodiment, the scope thereof is determined by the claims which follow.

What is claimed is:

1. A method of measuring bound chlorine concentration in volatile organic and inorganic samples comprising the steps of:

(a) exciting a noble gas to a metastable state for mixing with chlorine bound in a sample;

(b) reacting the excited noble gas to combine with chlorine in the sample to form excited chlorine molecules with the noble gas;

(c) permitting the excited noble chlorine molecules to decay by forming photons emitted from the decay; and (d) measuring the photons emitted by such excited chlorine molecules decay to quantify the amount of chlorine in the sample.

2. The method of claim 1 wherein the chlorine bound in the sample emit photons in the spectral region around 220 nanometers.

3. The method of claim 2 wherein the noble gas is excited for mixing with the chlorine of the sample in a chamber maintained at atmospheric pressure.

4. The method of claim 1 including the preliminary step of mixing krypton with helium, and placing the mixture of krypton and helium for exposure to an energy source to excite the krypton for subsequent decay from the excited state.

5. The method of claim 1 including:

(a) forming the noble gas from helium and an effective amount of krypton;

(b) reacting the noble gas at atmospheric pressure in a reaction chamber; and (c) measuring the emitted photons in the reaction chamber.

6. The method of claim 5 including the step of limiting the krypton to about 1% of the noble gas, and directed emitted photons through a reaction chamber window for measurement.

7. The method of claim 6 wherein the window directs the emitted photons to a measuring device passing through air.

8. An apparatus for detection of chemically bound chlorine in organic or inorganic compounds comprising:

(a) an excitation chamber for providing excitation energy therein;

(b) a noble gas supply for providing an effective amount above about 0.2 to about 1.0% of krypton in helium to said excitation chamber so that krypton molecules become excited therein;

(c) an input to said chamber for a sample having chemically bound chlorine therein; and (d) frequency sensitive light measuring sensor viewing said chamber for measuring light emitted therefrom on molecular interaction of chemically bound chlorine with krypton in said chamber.

9. The apparatus of claim 8 wherein said sensor measures light emitted from said chamber and passing through air to said sensor and thereby quantifies chlorine as a function of measured light.

10. The apparatus of claim 8 wherein said chamber operates at atmospheric pressure, and a window in said chamber enables light emitted in said chamber to be viewed through said window by said sensor.

11. A method of measuring chemically bound halides and determining the concentration thereof in samples wherein the method comprises the steps of:

(a) exciting a flow of krypton to an energy state above the ground energy state;

(b) mixing and reacting the excited krypton gas with chemically bound halides including chlorine compounds so that the chemically bound halides are changed to a high energy state on interaction with excited krypton to form krypton halide molecules which decay after formation to a ground energy state; and (c) measuring krypton halide decay from the excited state to determine the amount of halides in the sample.

12. The method of claim 11 including the step of separating as a function of frequency the decay of chlorine from fluorine.

13. The method of claim 11 including the step of detecting photons at about 222 nanometers.

14. The method of claim 11 including the preliminary step of mixing the krypton with helium and flowing the mixed helium and krypton into a reaction chamber;

mixing the chemically bound halides in the chamber with excited krypton to form krypton halide in the reaction chamber;

permitting the decay in the reaction chamber to emit photons for measurement;

directing the emitted photons through air to a measuring instrument.

15. The method of claim 14 wherein said reaction chamber is operated at atmospheric pressure, and said krypton comprises an effective amount of at least about 0.2% and helium comprises the remainder.

16. The method of claim 15 including the step of measuring photons in a frequency band capable of transmission through air.

17. The method of claim 11 including the step of exciting the krypton gas in the chamber by electric current flow therein, and decaying the krypton gas over a time interval to thereby charge the bound halides to the high energy state.

18. A method of measuring bound chlorine concentration in volatile organic and inorganic samples comprising the steps of:

(a) exciting helium to a metastable state;

(b) exciting a second noble gas from the decay of excited helium to a metastable state;

(c) reacting the excited second noble gas to combine with chlorine in the sample to form excited chlorine molecules with the excited second noble gas;

(d) permitting the excited chlorine molecules to decay by forming photons emitted from the decay; and (e) measuring the photons emitted by such decay to quantify the amount of chlorine in the sample.

19. The method of claim 18 including:

(a) mixing the helium and krypton as a gas flow into an excitation chamber;

(b) exposing the chamber to an excitation energy source;

(c) operating the chamber at atmospheric pressure;

(d) mixing a sample flow in the chamber;

(e) measuring the photons through an opening into the chamber.

20. The method of claim 19 wherein the krypton comprises at least about 0.2% of the helium, and the photons are transmitted through air.

21. The method of claim 20 wherein the energy source operates to from an electrical discharge.

22. A method of measuring bound fluorine and chlorine concentration in a vaporous sample comprising the steps of:

(a) forming a carrier gas primarily of helium and an effective amount of krypton gas above about 0.2%;

(b) flowing the carrier gas into an excitation chamber to excite the carrier gas including the step of forming at least some metastable helium and permitting time decay of the excited helium;

(c) forming metastable krypton gas in the carrier gas flow;

(c) reacting the metastable krypton with bound fluorine and chlorine to form metastable krypton fluorine and chlorine molecules;

(e) decaying over time the metastable molecules so that decay emits light photons in proportion to the bound fluorine and chlorine present in the sample.

23. The method of claim 22 including the preliminary step of time separating different bound fluorine and chlorine molecules and measuring photons to obtain time separated quantification thereof.

24. The method of claim 23 including the preliminary step of mixing up to about 1% krypton with helium and flowing the carrier gas into the excitation chamber at atmospheric pressure;

exciting the carrier gas in the chamber after introduction to from a specified concentration of metastable krypton gas; and decaying over time the krypton fluorine and chlorine molecules in the chamber to emit light photons transmitted out of the chamber for measurement on the exterior of said chamber.

25. The method of claim 24 including the preliminary step of time separating different bound fluorine and chlorine molecules in a chromatograph;

measuring from the exterior of said chamber light photons emitted from said chamber so that bound fluorine and chlorine molecules are quantified; and recording over time the quantified light photons to obtain the time separate bound fluorine and chlorine measurements.

* * * * *